US00PP20761P2

(12) United States Plant Patent
Briant

(10) Patent No.: US PP20,761 P2
(45) Date of Patent: Feb. 16, 2010

(54) ***LONICERA NITIDA* PLANT NAMED 'BRILIAME'**

(50) Latin Name: *Lonicera nitida*
Varietal Denomination: Briliame

(75) Inventor: André Briant, St.-Barthélémy d'Anjou (FR)

(73) Assignee: Selection New Plant SARL, Le Luc en Provence (FR)

( * ) Notice: Subject to any disclaimer, the term of this patent is extended or adjusted under 35 U.S.C. 154(b) by 0 days.

(21) Appl. No.: 12/219,779

(22) Filed: Jul. 28, 2008

(51) Int. Cl.
*A01H 5/00* (2006.01)

(52) U.S. Cl. ..... Plt./226
(58) Field of Classification Search ..... Plt./226
See application file for complete search history.

*Primary Examiner*—Susan B McCormick Ewoldt
(74) *Attorney, Agent, or Firm*—Buchanan Ingersoll & Rooney PC

(57) ABSTRACT

A new and distinct *Lonicera nitida* cultivar is provided that is a mutation of the 'Briloni' cultivar (U.S. Plant Pat. No. 15,234). Distinctive yellow-green new foliage is formed that bears less yellow coloration than the 'Briloni' cultivar. A somewhat creeping growth habit is displayed. The foliage of the plant well resists burning when exposed to full sun. The unusual yellow-green foliage coloration combined with the other characteristics provides the horticultural industry with an distinctive ornamental plant for growing in pots or in the landscape.

1 Drawing Sheet

Botanical/commercial classification: *Lonicera nitida*/ Lonicera Plant.

Varietal denomination: cv. Briliame.

SUMMARY OF THE INVENTION

The present invention comprises a new and distinct cultivar of *Lonicera nitida*, and hereafter is referred to by the cultivar name 'Briliame'. Plants of this species sometimes are called Box Honeysuckle.

A single plant possessing the characteristics of the new cultivar was discovered during July 2004 at Saint-Barthélémy d'Anjou, Maine et Loire, France while growing among a block of plants of the 'Briloni' cultivar (U.S. Plant Pat. No. 15,234). The new cultivar of the present invention is believed to be a spontaneous mutation of the 'Briloni' cultivar of unknown causation. I was attracted to the new cultivar primarily because of its distinctive foliage coloration that differed from that of the parental cultivar. Had the plant of this new cultivar not been discovered and preserved it would have been lost to mankind.

It was found that the new *Lonicera nitida* plant displays the following combination of characteristics:

(a) forms attractive new foliage that well resists burning when exposed to full sun and bears yellow-green coloration with less yellow coloration than the 'Briloni' cultivar (U.S. Plant Pat. No. 15,234), (b) possesses a somewhat creeping growth habit, and (c) provides attractive ornamentation.

The new cultivar of the present invention readily can be distinguished from its parent 'Briloni' cultivar in view of the presence of less yellow coloration on the new yellow-green foliage. Also, the new cultivar of the present invention can be readily distinguished from the 'Maigrün' cultivar (non-patented in the United States) since the 'Maigrün' cultivar generally exhibits greener foliage. Additionally, the new cultivar of the present invention can be readily distinguished from the 'Braggeen's Gold' cultivar (non-patented in the United States) upon an inspection of the growth habit. More specifically, the growth habit of the 'Baggeen's Gold' cultivar is upright unlike the somewhat creeping growth habit of the new cultivar.

Asexual reproduction of the new cultivar by the use of cuttings as performed at Saint-Barthélémy d'Anjou, Maine et Loire, France, has demonstrated that the characteristics of the new cultivar are firmly fixed and are retained through successive generations of asexual propagation. Accordingly, the new cultivar can be asexually reproduced in a true-to-type manner.

The new cultivar well meets the needs of the horticultural industry and can be used to provide attractive ornamentation when grown in pots or in the landscape.

BRIEF DESCRIPTION OF THE PHOTOGRAPHS

The accompanying photographs depict typical plants of the new cultivar while being grown outdoors at Saint-Barthélémy d'Anjou, Maine et Loire, France, with color being shown as true as is reasonably possible in color illustrations of this character. Such plants were approximately three years of age and had been asexually reproduced through the use of cuttings.

DETAILED DESCRIPTION

Figure 1:
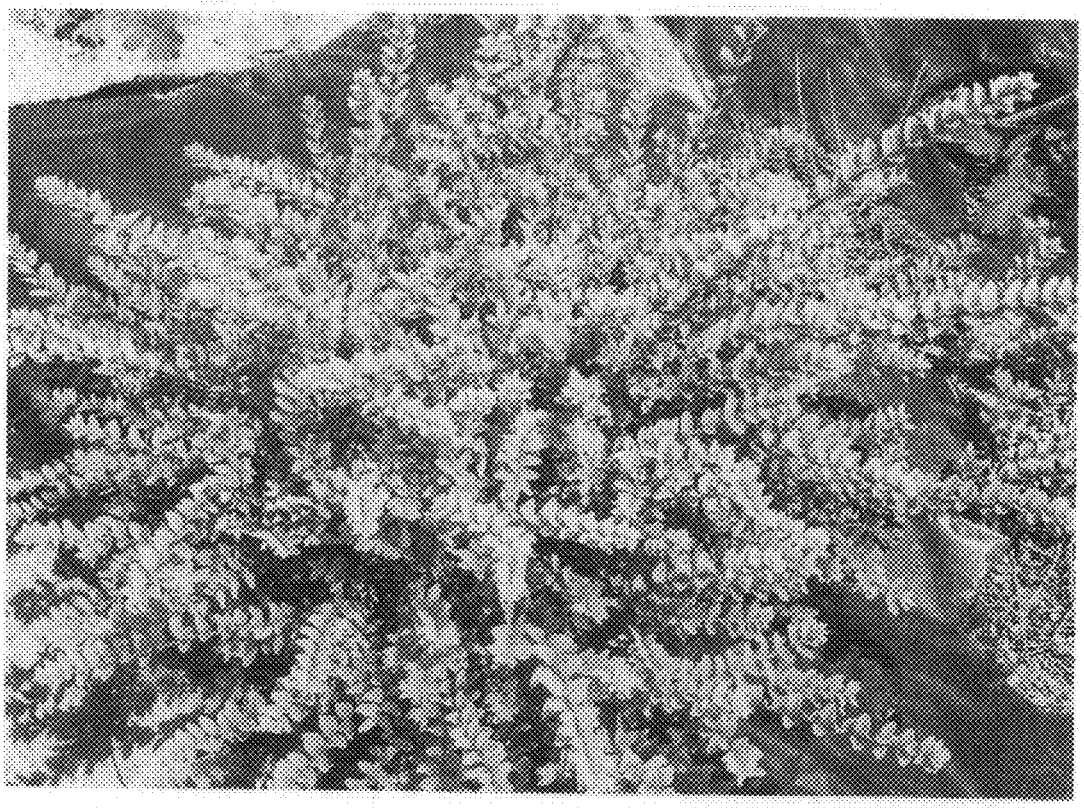
FIG. 1 shows an overall view of a typical plant of the new cultivar wherein the somewhat creeping growth habit is apparent.
Figure 2:
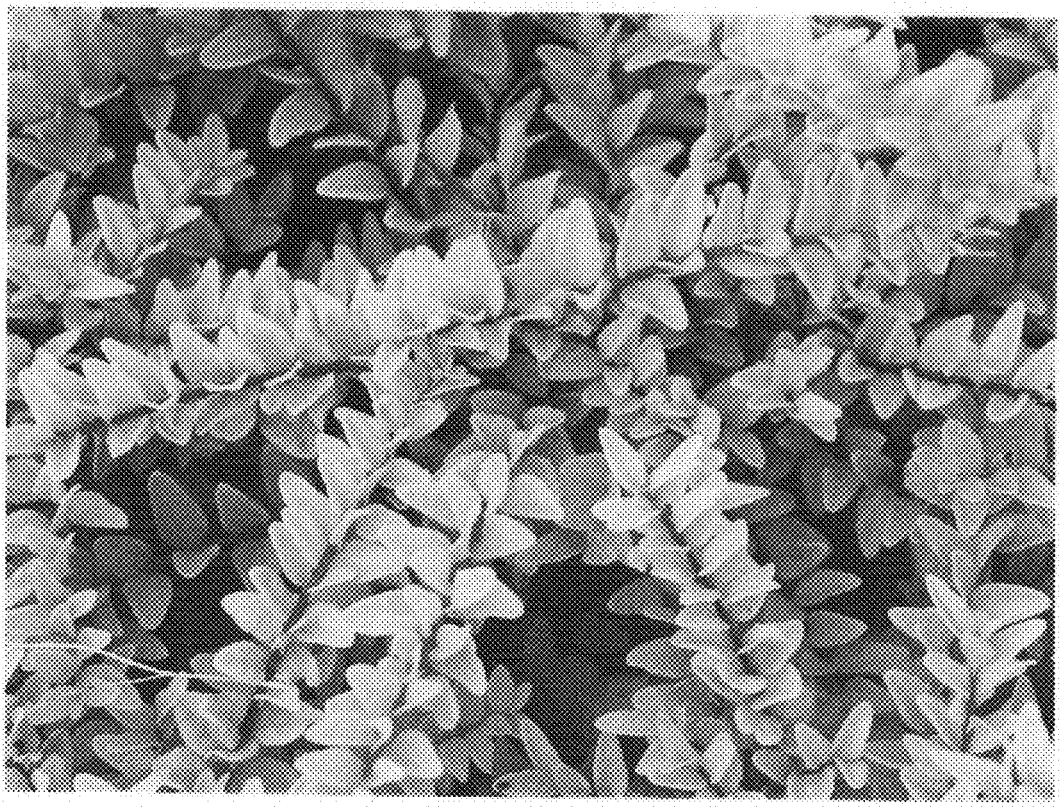
FIG. 2 shows a close view of the attractive yellow-green foliage of the new cultivar.

The plants were approximately three years of age and were observed during May when grown outdoors at Saint-Barthélémy d'Anjou, Maine et Loire, France. Such plants had been asexually reproduced by the use of cuttings. Color terminology is with reference to the R.H.S. Colour Chart of The Royal Horticultural Society, London. Common color terms are to be accorded their customary dictionary significance.

Origin: Spontaneous mutation of the 'Briloni' cultivar (U.S. Plant Pat. No. 15,234).

Plant:

*Form.*—Somewhat creeping.

*Height.*—Approximately 45 cm on average.

*Width.*—Approximately 60 cm on average.

Branches:

*Length.*—Commonly approximately 50 to 60 cm on average.

*Color.*—Young Stems: on the upper surface near Greyed-Purple Group 187A, and on the under surface near Yellow-Green Group 145A. Adult Wood: near Greyed-Green Group 197B.

Foliage:

*Shape.*—Generally ovoid.

*Length.*—Approximately 1.8 cm on average.

*Width.*—Approximately 1.1 cm on average.

*General appearance.*—Dense and clear.

*Color.*—New Foliage: Upper Surface: Commonly near Yellow-Green Group 144B toward the base, and near Yellow Group 9A at the tip. Under Surface: Commonly near Yellow-Green Group 144B toward the base, and near Yellow Group 6B at the tip. Mature Foliage: Upper Surface: Commonly near Green Group 137A. Under Surface: commonly near Yellow-Green Group 146C.

*Petiole.*—Approximately 1.5 mm in length on average, smooth on both surfaces, near Yellow-Green Group 144B in coloration on the upper surface, and near Yellow-Green Group 144C on the under surface.

Inflorescence:

*Peduncle.*—Commonly approximately1 mm in length and width, and near Yellow-Green Group 144B in coloration.

*Time of flowering.*—May.

*Bloom period.*—Approximately three weeks on average.

*Type.*—Inconspicuous.

*Size.*—Approximately 5 mm in diameter.

*Configuration.*—Tubular, typical of the *nitida* species, and commonly with 5 joined petals.

*Texture.*—Slightly granular petals.

*Color.*—On the upper surface near Green-Yellow Group 1D commonly with a tiny spot of near Yellow Group 2C, and on the under surface near Green-Yellow Group 1D.

*Fragrance.*—None.

*Stamen.*—Five in number, and arranged around the pistil.

*Anthers.*—Approximately 1 mm in size, and near Green-Yellow Group 1D in coloration.

*Filaments.*—Approximately 9 mm in length on average, and near Yellow Group 4C in coloration.

*Pollen.*—Near Yellow Group 4C in coloration.

*Pistil.*—One in number.

*Styles.*—Approximately 8 mm in length on average, and near Yellow Group 4D in coloration.

*Stigma.*—Approximately 1 mm in size, and near Yellow Group 5C in coloration.

*Hips.*—Generally smooth, substantially round, approximately 4 to 5 mm in diameter on average, and near Violet Group 88B in coloration.

*Receptacle.*—Commonly approximately 1 mm in length and width, and near Yellow-Green Group 144B in coloration.

During observations to date, no particular disease or pest problems have been encountered when growing the new cultivar of the present invention.

Plants of the new 'Briliame' cultivar have not been observed under all possible environmental conditions to date. Accordingly, it is possible that the phenotypic expression may vary somewhat with changes in light intensity and duration, cultural practices, and other environmental conditions.

I claim:

1. A new and distinct *Lonicera nitida* plant that exhibits the following combination of characteristics:

(a) forms attractive new foliage that well resists burning when exposed to full sun and bears yellow-green coloration with less yellow coloration than the 'Briloni' cultivar (U.S. Plant Pat. No. 15,234), (b) possesses a somewhat creeping growth habit, and (c) provides attractive ornamentation;

substantially as illustrated and described.

* * * * *